US007563621B2

(12) United States Patent
Profitt et al.

(10) Patent No.: US 7,563,621 B2
(45) Date of Patent: Jul. 21, 2009

(54) ABSORBING ORGANIC REAGENTS INTO DIAGNOSTIC TEST DEVICES BY FORMATION OF AMINE SALT COMPLEXES

(75) Inventors: James A Profitt, Goshen, IN (US); Alexander H. Orn, Nappanee, IN (US)

(73) Assignee: Siemens Healhcare Diagnostics Inc, Tarrytown, NY (US)

( * ) Notice: Subject to any disclaimer, the term of this patent is extended or adjusted under 35 U.S.C. 154(b) by 288 days.

(21) Appl. No.: 10/506,098

(22) PCT Filed: Feb. 17, 2003

(86) PCT No.: PCT/IB03/00641

§ 371 (c)(1),
(2), (4) Date: Aug. 30, 2004

(87) PCT Pub. No.: WO03/075008

PCT Pub. Date: Sep. 12, 2003

(65) Prior Publication Data
US 2005/0106748 A1 May 19, 2005

(51) Int. Cl.
G01N 33/48 (2006.01)
(52) U.S. Cl. ............................. 436/166; 422/56; 422/57
(58) Field of Classification Search .................. 422/56, 422/58, 61, 68.1; 436/164, 166
See application file for complete search history.

(56) References Cited

U.S. PATENT DOCUMENTS

| 3,438,737 | A |   | 4/1969 | Atkinson | 23/230 |
|---|---|---|---|---|---|
| 3,485,587 | A |   | 12/1969 | Keston | 23/230 |
| 4,440,724 | A | * | 4/1984 | Tabb et al. | 422/56 |
| 5,057,276 | A | * | 10/1991 | Helling et al. | 422/56 |
| 5,066,462 | A |   | 11/1991 | Kawasaki et al. | 422/56 |
| 5,077,222 | A |   | 12/1991 | Lau | 436/88 |
| 5,087,575 | A |   | 2/1992 | Lau | 436/166 |
| 5,183,742 | A |   | 2/1993 | Omoto et al. | 435/14 |
| 5,279,790 | A |   | 1/1994 | Corey et al. | 422/55 |
| 5,286,454 | A |   | 2/1994 | Nilsson et al. | 422/102 |
| 5,399,498 | A |   | 3/1995 | Pugia | 436/86 |
| 5,424,125 | A |   | 6/1995 | Ballard et al. | 428/364 |
| 5,585,069 | A |   | 12/1996 | Zanzucchi et al. | 422/100 |
| 5,593,895 | A |   | 1/1997 | Cahill et al. | 436/86 |
| 5,716,851 | A |   | 2/1998 | Pugia et al. | 436/86 |
| 5,750,405 | A |   | 5/1998 | Albarella et al. | 436/88 |
| 5,837,200 | A |   | 11/1998 | Diessel et al. | 422/73 |
| 5,908,787 | A | * | 6/1999 | Cast et al. | 436/86 |
| 5,922,283 | A |   | 7/1999 | Hsu | 422/56 |
| 5,922,615 | A |   | 7/1999 | Nowakowski et al. | 436/518 |
| 5,942,443 | A |   | 8/1999 | Parce et al. | 436/6 |
| 6,042,709 | A |   | 3/2000 | Parce et al. | 204/453 |
| 6,074,725 | A |   | 6/2000 | Kennedy | 428/188 |
| 6,086,740 | A |   | 7/2000 | Kennedy | 204/601 |
| 6,090,251 | A |   | 7/2000 | Sundberg et al. | 204/453 |
| 6,150,180 | A |   | 11/2000 | Parce et al. | 436/514 |
| 6,815,210 | B1 | * | 11/2004 | Profitt et al. | 436/86 |

FOREIGN PATENT DOCUMENTS

| EP | 0574769 A1 | 12/1993 | 33/52 |
|---|---|---|---|
| EP | 0877251 A1 | 11/1998 | 33/52 |
| EP | 1160571 A1 | 12/2001 | 33/52 |
| JP | 04361160 | 12/1992 | 33/68 |
| WO | 03/001213 A2 | 1/2003 | 33/68 |

OTHER PUBLICATIONS

"The Performance of a Total Protein Urinalysis Strip Based on a Novel Dye System," Profit, J.; Pugia, M.; Wallace, J.; Newman, D.; D'Mello, L.; Cast, T.; Orn, A.; (Poster Presentation) *American Society of Nephrology Meeting*, 2001, San Francisco.
"The Performance of a Total Protein Urinalysis Strip Based on a Novel Dye System," Newman, D.; Profitt, J.; Pugia, M.; D'Mello, L.; Cast, T.; Orn, A.; (Abstract), *Journal of the American Society of Nephrology*, Sep. 2001, vol. 12, pp. 118A-119A. (Abstract for Reference C01).
"Technology Behind Diagnostic Reagent Strips," Pugia, M., *Laboratory Medicine*, 2000, vol. 31, pp. 92-96.
"Measurement of the Albumin Content of Urinary Protein Using Dipsticks," Sasaki, M.; Pugia, M.; Parker, D.; Kuromoto, K.; Furukawa, I.; Konishi, I.; *Journal of Clinical Laboratory Analysis*, 1999, vol. 13, No. 5, pp. 246-250.
"High-Sensitivity Dye Binding Assay for Albumin in Urine," Pugia, M.; Lott, J.; Profitt, J.; Cast, T.; *Journal of Clinical Laboratory Analysis*, 1999, vol. 13, No. 4, pp. 180-187.
"Screening School Children for Albuminaria, Proteinuria and Occult Blood with Dipsticks," Pugia, M; Lott, J.; Kajima, J.; Saambe, T.; Sasaki, M.; Kuromoto, K.; Nakamura, R.; Fusegawa, H.; and Ohta, Y.; *Clinical Chemistry and Laboratory Medicine*, 1999, vol. 27, pp. 49-57.

(Continued)

*Primary Examiner*—Lyle A Alexander
(74) *Attorney, Agent, or Firm*—Harold N. Wells

(57) ABSTRACT

A method of applying an organic acid reagent having limited transolubility in organic solvents, aqueous solvents, and mixtures thereof to a component of a diagnostic test device by mixing an organic acid reagent and an amine to form a salt complex, dissolving the salt complex in a solvent to release the organic acid reagent into the solvent, and applying the solvent to the component of the diagnostic test device such that the organic acid reagent present in the solvent becomes integrated into the diagnostic test device. The amine is represented by the formula $H_mNR_n$ wherein m is 0, 1, or 2; n is 1, 2, or 3; the sum of m and n is 3; and R is an independently selected group which renders the salt complex soluble in aqueous solvents, organic solvents, or mixtures thereof. The amine is also represented by the formula $NR_4^+$ wherein R is an independently selected group which renders the salt complex soluble in aqueous solvents, organic solvents, or mixtures thereof. The organic acid reagent is selected from a carboxylic acid, a sulfonic acid, a phosphoric acid, and mixtures thereof. Preferred reagents are dyes like pyragallol red. In a specific embodiment the diagnostic test device is a paper test strip.

24 Claims, No Drawings

OTHER PUBLICATIONS

"The Relative Utility of Urinary Total Protein and Albumin Dipstick Measurement in the Identification of Patients with Myleoma and Tubular Proteinuria," Profitt, J.; Pugia, M.; Wallace, J.; Newman, D.; D'Mello, L.; (Poster Presentation) *Clinical Nephrology Meetings 2001*, National Kidney Foundation, Apr. 2001.

"Comparison of Instrument-Read Dipsticks for Albumin and Creatinine in Urine with Visual Results and Quantitative Methods," Pugia, M.; Lott, J.; Luke, K.; Shihabi, Z.; Wians, F.; Phillips, L.; *Journal of Clinical Laboratory Analysis*, 1998, vol. 12, No. 5, pp. 280-284.

"Comparison of Ion-Pair and Amide-Based Column Reversed-Phase Liquid Chromatography for the Separation of Thiamine-Related Compounds," Vinas, P.; Lopez-Erroz, C.; Balsalobre, N.; Hernandez-Cordoba, M.; *Journal of Chromatography B*, 2001, vol. 757, pp. 301-308, Elsevier Science B.V.

"Direct Determination of Sinigrin in Mustard Seed without Desulfatation by Reversed-Phase Ion-Pair Liquid Chromatography," Jen, J-F.; Lin, T-H.; Huang, J-W.; Chung, W-C.; *Journal of Chromatography A*, 2001, vol. 912, pp. 363-368.

"On-Chip Integration of Neutral Ionophore-Based Ion Pair Extraction Reaction," Hisamoto, H; Horiuchi, T.; Tokeshi, M.; Hibara, A; Kitamori, T.; *Analytical Chemistry*, 2001, vol. 73, No. 6, pp. 1382-1386.

"Rapid And Simultaneous Determination Of Mycophenolic Acid And Its Glucuronide Conjugate In Human Plasma By Ion-Pair Reversed-Phase High-Performance Liquid Chromatography Using Isocratic Elution," Hosotsubo, H.; Takahara, S.; Kokado, Y.; Permpongkosol, S.; Wang, J-D.; Tanaka, T.; Matsumiya, K.; Kitamura, M.; Okuyama, A.; Sugimoto, H.; *Journal of Chromatography B*, 2001, vol. 753, pp. 315-320.

"Determination Of Aromatic Sulfonates In Coastal Water By On-Line Ion-Pair Solid-Phase Extraction/Ion-Pair Liquid Chromatography With UV Detection," Gimeno, R.A.; Marce, R.M.; Borrull, F.; *Chromatographia*, 2001, vol. 53, No. 1/2, pp. 22-26, Friedrich Vieweg & Sohn Verlasgsgesellschaft mbH.

"Ion-Pair Formation As A Strategy To Enhance Topical Delivery Of Salicylic Acid," Megwa, S.A.; Cross, S.E.; Benson, H.A.E.; Roberts, M.S.; *Journal of Pharmacy and Pharmacology*, 2000, vol. 52, No. 8, pp. 919-928, Pharmaceutical Society of Great Britain.

"Hydrophobic Ion Pair Formation between Leuprolide and Sodium Oleate for Sustained Release from Biodegradable Polymeric Microspheres," Choi, S.H.; Park, T.G.; *International Journal of Pharmaceutics*, 2000, vol. 203, No. 1/2, pp. 193-202, Elsevier Science B.V.

"Interpretation by the Solvophobic Theory on the Linear Additive Representation of the Logarithm of Ion-Pair Extraction Constant with Individual Contributions of Cation, Anion, and Organic Solvent," Miyabe, K.; Taguchi, S.; Kasahara, I.; Goto, K.; *Journal of Physical Chemistry B*, 2000, vol. 104, No. 35, pp. 8481-8490.

"Merocyanine 540 Solubilized as an Ion Pair with Cationic Surfactant In Nonpolar Solvents: Special And Photochemical Properties," Bilski, P.; McDevitt, T.; Chignell, C.F.; *Photochemistry and Photobiology*, 1999, vol. 69, No. 6, pp. 671-676.

"Screening for Proteinuria in Japanese Schoolchildren: A New Approach," Pugia, M.; Murakami, M.; Lott, J.; Ohta, Y.; Kitagawa, T.; Yamauchi, K.; Suhara, Y.; Kasjima, J.; *Clinical Chemistry and Laboratory Medicine*, 2000, vol. 38, 7 pages.

"Conductometric Investigation of Dye-Surfactant Ion Pair Formation in Aqueous Solution," Bracko, S.; Span, J.; *Dyes and Pigments*, 2000, vol. 45, No. 2, pp. 97 (abstract only).

* cited by examiner

ABSORBING ORGANIC REAGENTS INTO DIAGNOSTIC TEST DEVICES BY FORMATION OF AMINE SALT COMPLEXES

FIELD OF THE INVENTION

The invention relates to methods for absorbing an organic reagent into a component of a diagnostic test device and diagnostic test devices prepared by such methods. In particular, the invention relates to methods for absorbing an organic reagent into the absorbent material of a diagnostic test strip and diagnostic test strips prepared by such methods.

BACKGROUND OF THE INVENTION

The use of diagnostic test devices such as dry devices to analyze components in a sample of human body fluid such as urine is well known. A diagnostic test strip is one type of dry device that may be used to analyze components in human body fluid. Diagnostic test strips are typically composed of one or more pads of paper attached to a plastic carrier which serves as a handle.

With diagnostic test strips, a reagent such as an organic molecule is applied to or absorbed into an absorbent material such as paper by dipping the absorbent material into one or more solvent systems containing one or more reagents. Upon dipping the absorbent material into the solvent system, the reagent contained in the solvent system becomes absorbed within or integrated into the fibers of the absorbent material. Once the reagent has been applied to the absorbent material, the absorbent material is dried and assembled into a test strip.

The dried test strip containing the reagent can then be used to test for the presence of an analyte(s) in test samples. Test samples are typically human urine or other biological fluids. Test strips are frequently used to detect proteins in protein assays also referred to as total protein tests or proteinuria tests or to test for the presence of particular proteins in conditions such as albuminuria. Examples of analytes which are tested include, but are not limited to, proteins, hormones, drugs, metabolites, glucose, protons (i.e., for pH), ions (i.e., specific gravity), and blood cells. To test for the presence of an analyte(s), the test strip is dipped into the test sample at which point the reagent in the test strip participates in a reaction sequence with a particular analyte(s) in the test sample. Upon detecting the presence of a particular analyte(s) in the test sample, the reagent in the test strip responds with an instrumentally or visually detectable signal to the user such as a change in color.

In order for a reagent to become applied to the absorbent material of a diagnostic test device such as a test strip, the reagent needs to be soluble in the solvent system used to apply the reagent to the absorbent material. The more soluble the reagent is in this solvent system, the more reagent becomes applied to the absorbent material and the richer the color obtained on the absorbent material. A high concentration of reagent in the absorbent material often allows a rich color indication.

In order for a reagent which has been absorbed into the absorbent material of a diagnostic test device such as a test strip to be used to detect an analyte(s) in a test sample, the reagent that is trapped within the fibers of the absorbent material typically needs to be sufficiently soluble to be available to interact with the analyte(s) in the test sample. That is, the reagent that has been absorbed into the absorbent material typically needs to be soluble in the final test strip environment (i.e., the test sample) for solution chemistry to take place and to give an indication that a particular analyte(s) is present in the test sample. However, high solubility of the reagent in the test sample may be undesirable in some systems as problems such as reagent migration between multiple pads on the test strip can occur. An optimal system would allow assay designers to control the degree of reagent solubility in the test sample.

The organic reagents which are typically applied to the absorbent material of diagnostic test devices are either soluble in aqueous solvents with no solubility or only limited solubility in organic solvents or are soluble in organic solvents with no solubility or only limited solubility in aqueous solvents. In other words, many of these organic reagents have no transolubility or only limited transolubility in organic and aqueous solvents. The lack of transolubility of these reagents in organic and aqueous solvents has made the application of certain reagents to diagnostic test devices and the use of the diagnostic test devices containing these reagents difficult.

To illustrate, a solubility problem arises where an organic reagent must be applied to the absorbent material of diagnostic test devices using an organic solvent because the reagent is readily soluble only in organic solvents, but the reagent must subsequently be used to detect the presence of proteins in an aqueous test sample (i.e., urine) in which the reagent has no solubility or only limited solubility. For example, pyrogallol red is a dye commonly used in diagnostic protein tests that is soluble in organic solvents such as methanol but has no solubility or only limited solubility in aqueous solvents such as water or urine. One challenge facing assay designers has been to find a way to apply a reagent such as pyrogallol red to test strips via an aqueous solvent and to then use the reagent to detect the presence of proteins in an aqueous test sample in which the reagent has controlled solubility.

One method that has been used to dissolve organic reagents having limited transolubility in organic and aqueous solvents has been to increase the alkalinity of the aqueous solvent. This approach has been used to dissolve pyrogallol red dye in aqueous solvents and apply the dye via the aqueous solvent to the absorbent material such as the test paper. Although pyrogallol red may be applied to a diagnostic test device such as a test strip via an aqueous solvent using this approach, the strongly alkaline aqueous solvent needed to dissolve the pyrogallol red causes an unacceptable variation in the color of the test paper, rendering the paper unusable in diagnostic tests.

Another method used to dissolve organic reagents having limited transolubility in organic and aqueous solvents has been to add water miscible cosolvents, such as alcohols, to the solvent system. This approach also has shortcomings. The addition of a water miscible cosolvent may increase the solubility of one component in the solvent system but may simultaneously decrease the solubility of other component(s). In addition, the amount and type of water miscible cosolvent typically requires careful selection, often through a trial and error process, to increase the solubility of the organic reagent while maintaining the solubility of the water soluble components.

Because different reagents have varying degrees of solubility in the solvents used to apply reagents to the absorbent materials of diagnostic test devices such as test papers, it is sometimes necessary to use a multiple-dip or multiple-step application process. For example, a multiple-dip application process may be used where the desired reagents are reactive with each other or with one or more components contained in one of the solvent systems. Another challenge facing assay designers has been to find a way to control the transolubility of a reagent(s) where a multiple dip application process is involved. For example, in a two-dip application process, a reagent may be applied to a test paper using an aqueous solvent as the first dip solution, yet it is desirable that the reagent remain insoluble in the second, organic dip solution to prevent leaching of the reagent into the second dip solution that is being applied to the test paper.

For the foregoing reasons, there exists a need for a method to apply reagents having limited transolubility in organic solvents, aqueous solvents, and mixtures thereof to diagnostic test devices such as diagnostic test strips via organic solvents, aqueous solvents, and mixtures thereof for subsequent use in detecting the presence of an analyte(s) in test samples such as aqueous test samples. There also exists a need for a method to apply reagents having limited transolubility in organic solvents, aqueous solvents, and mixtures thereof to diagnostic test devices via organic solvents, aqueous solvents, and mixtures thereof (a) without adding, or with reduced need to add, cosolvents which affect the solubility of other components in the solvent and (b) without subjecting the reagent to harsh chemical conditions to dissolve the reagent in the desired solvent. A need also exists for a method to control the transolubility of a reagent(s) where a multiple dip application process is involved without side effects such as leaching of the reagent into subsequent dip solutions. There is also a need for a method to apply reagents to diagnostic test devices which allows assay designers to generally control or choose the degree of reagent solubility in the test sample. There also exists a need for diagnostic test strips which can be prepared without the above noted shortcomings and with the above noted advantages.

SUMMARY OF THE INVENTION

According to one embodiment, an organic acid reagent having limited transolubility in organic solvents, aqueous solvents, and mixtures thereof is applied to a component of a diagnostic test device by mixing an organic acid reagent and an amine to form a salt complex; dissolving the salt complex in a solvent to release the organic acid reagent into the solvent; and applying the solvent to the component of the diagnostic test device such that the organic acid reagent present in the solvent becomes integrated into the diagnostic test device. The amine is represented by the formula $$H_mNR_n$$

wherein m is 0, 1, or 2; n is 1, 2, or 3; the sum of m and n is 3; and R is an independently selected group which renders the salt complex soluble in aqueous solvents, organic solvents, or mixtures thereof.

According to another embodiment, an organic reagent having limited transolubility in organic solvents, aqueous solvents, and mixtures thereof is applied to a component of a diagnostic test device by mixing an organic reagent and an amine to form a salt complex; dissolving the salt complex in a solvent to release the organic reagent into the solvent; and applying the solvent to the component of the diagnostic test device such that the organic reagent present in the solvent becomes integrated into the diagnostic test device. The amine is selected from trimethylamine, triethylamine, tributyl amine, trioctylamine, tris(hydroxymethyl)aminomethane, aminoethanol, butylamine, octylamine, triethanolamine, glucamine, a polyethyleneglycolamine, an amino acid, and mixtures thereof.

According to a further embodiment, an organic acid reagent having limited transolubility in organic solvents, aqueous solvents, and mixtures thereof is applied to a paper of a diagnostic test strip by mixing an amine and an organic acid reagent to form a salt complex; dissolving the salt complex in a solvent to release the organic acid reagent into the solvent; and applying the solvent to the paper of the diagnostic test strip such that the organic acid reagent present in the solvent becomes integrated into the paper. The amine is selected from trimethylamine, triethylamine, tributyl amine, trioctylamine, tris(hydroxymethyl)aminomethane, aminoethanol, butylamine, octylamine, triethanolamine, glucamine, a polyethyleneglycolamine, an amino acid, and mixtures thereof, and the organic acid reagent is selected from a carboxylic acid, a sulfonic acid, a phosphoric acid, and mixtures thereof.

According to a still further embodiment, an organic acid reagent having limited transolubility in organic solvents, aqueous solvents, and mixtures thereof is applied to a component of a diagnostic test device by combining an ionized organic acid reagent and a quaternary ammonium ion by an ion exchange process to form a salt complex; dissolving the salt complex in a solvent to release the organic acid reagent into the solvent; and applying the solvent to the component of the diagnostic test device such that the organic acid reagent present in the solvent becomes integrated into the diagnostic test device. The ammonium ion is represented by the formula $$NR_4^+$$

wherein R is an independently selected group which renders the salt complex soluble in aqueous solvents, organic solvents, or mixtures thereof.

According to a still further embodiment, a diagnostic test device containing an organic acid reagent having limited transolubility in organic solvents, aqueous solvents, and mixtures thereof is prepared by mixing an organic acid reagent and an amine to form a salt complex; dissolving the salt complex in a solvent to release the organic acid reagent into the solvent; and applying the solvent to a component of the diagnostic test device such that the organic acid reagent present in the solvent becomes integrated into the diagnostic test device. The amine is represented by the formula $$H_mNR_n$$

wherein m is 0, 1, or 2; n is 1, 2, or 3; the sum of m and n is 3; and R is an independently selected group which renders the salt complex soluble in aqueous solvents, organic solvents, or mixtures thereof.

According to a still further embodiment, a diagnostic test device containing an organic acid reagent having limited transolubility in organic solvents, aqueous solvents, and mixtures thereof is prepared by combining an ionized organic acid reagent and a quaternary ammonium ion by an ion exchange process to form a salt complex; dissolving the salt complex in a solvent to release the organic acid reagent into the solvent; and applying the solvent to a component of the diagnostic test device such that the organic acid reagent present in the solvent becomes integrated into the diagnostic test device. The ammonium ion is represented by the formula $$NR_4^+$$

wherein R is an independently selected group which renders the salt complex soluble in aqueous solvents, organic solvents, or mixtures thereof.

The above summary of the present invention is not intended to represent each embodiment, or every aspect, of the present invention. This is the purpose of the detailed description which follows.

DESCRIPTION OF EMBODIMENTS OF THE INVENTION

Embodiments of the invention are, in part, based on the discovery that reagents having limited transolubility in organic solvents, aqueous solvents, and mixtures thereof may be applied to an absorbent component(s) of a diagnostic test device such as a diagnostic test strip via organic solvents, aqueous solvents, and mixtures thereof and may subsequently be used to detect the presence of an analyte(s) in organic test samples, aqueous test samples, and mixtures thereof. Reagent(s) having limited transolubility may be applied to diagnostic test devices via organic solvents, aqueous solvents, and mixtures thereof using the methods described herein (a) without adding, or with reduced need to add, cosolvents which affect the solubility of other components in the solvent and (b) without subjecting the reagent to harsh chemical conditions to dissolve the reagent in the desired solvent. The transolubility of a reagent(s) in the final test sample may be generally controlled using the methods described herein. In addition, the transolubility of a reagent(s) may be generally controlled using the methods described herein where a multiple dip application process is used without side effects such as the reagent leaching into subsequent dip solutions.

It has been discovered that by mixing an amine having certain properties with an organic acid reagent having no transolubility or only limited transolubility in organic solvents, aqueous solvents, and mixtures thereof, a salt complex is formed which can be dissolved in organic solvents, aqueous solvents, and mixtures thereof. The salt complex can then be absorbed into one or more components of a diagnostic test device such as an absorbent material via organic solvents, aqueous solvents, and mixtures thereof. By forming a salt complex to absorb the organic reagent into the component(s) of the diagnostic test device, the organic reagent can be applied to the component(s) evenly, homogeneously and in a controlled fashion.

As used herein, the term "transolubility" indicates that the reagent is soluble in more than one of the following three types of solvents: aqueous solvents, non-aqueous solvents such as organic solvents, and mixtures of aqueous and non-aqueous solvents as opposed to being soluble in only one or none of these three types of solvents. Transolubility may be achieved by selecting an appropriate counterion for the reagent of interest.

Suitable diagnostic test device formats for use in embodiments of the invention include, but are not limited to, dry devices such as test strips, wands, sticks, tubes, chips, channels, wells, cavities, grids, wafers, disks, plates, and cartridges where reagent is applied as dried films, layers, spots, or arrays of spots on an absorbent material composing the device or on an absorbent material component within or attached to the dry device. Examples of suitable absorbent materials include, but are not limited to, papers, fibers, fabrics, non-woven fiber mats, felts, porous membranes, porous ceramics, porous hydrophilic plastics, porous sponges, hygroscopic gels, hygroscopic polymers, and porous or hygroscopic natural materials. Two examples of suitable papers are Ahlstrom 204 available from Ahlstrom Technical Specialties in Mt. Holly Springs, Pa. and Whatman 3MM available from Whatman Inc. in Ann Arbor, Mich., both of which are made from cellulose. The methods described herein also allow reagent solution to be used in a manual or automated diagnostic assay system as a stable liquid, for example, in a reagent container as part of a diagnostic test kit.

Other suitable formats for the diagnostic test devices for use in embodiments of the invention include, but are not limited to, wires, fibers, wands, sticks, tubes, chips, channels, wells, cavities, grids, wafers, disks, plates, chambers, capsules, and cartridges of glass, non-porous ceramics, plastics, silicones, silicon, other semi-conductors, metals, and coated papers which may use shape or structure rather than an absorbent material to hold a reagent. It is also contemplated that the diagnostic test devices may be microscale fluidic devices and microfluidic assay platforms for performing clinical diagnostics such as, but not limited to, disks, chips, "labs on disks", "labs on chips", "labs on CDs", microchannels, microlaboratory arrays, and microlaboratory disks. Such formats may supplement and/or be used in place of the dry device formats described above. For example, rather than using the methods described herein to absorb an organic reagent into absorbent materials such as papers and building test strips with these papers, it is contemplated that these papers may instead be formed into small patches which can be installed into chip devices. It is also contemplated that the solutions of organic reagents which may be applied to the absorbent materials as described herein may instead be dried onto or injected into defined areas of the diagnostic test units.

Where diagnostic test strips are employed, the test strips may be made from a variety of materials and are typically made from one or more pads of paper which are cut and attached to a polymeric or plastic carrier to form the diagnostic strip. Pads for test strips may be made from other woven, nonwoven, patterned, or cast materials including natural and synthetic materials which are capable of absorbing fluid such as polyester, nitrocellulose, ceramics, and glass fiber.

The process described herein involves (a) mixing an amine having lipophilic properties, hydrophilic properties, or both lipophilic and hydrophilic properties with an organic acid reagent having no transolubility or only limited transolubility in organic solvents, aqueous solvents, and mixtures thereof to form a salt complex; (b) dissolving the salt complex in an organic solvent, an aqueous solvent, or mixtures of one or more organic solvents and one or more aqueous solvents to release the reagent into the solvent; and (c) applying the solvent containing the reagent to a component of a diagnostic test device so that the reagent present in the solvent becomes integrated into the diagnostic test device. For example, the solvent containing the reagent may be applied to the diagnostic test device by dipping an absorbent component or material such as paper into the solvent so that the reagent which is dissolved in the solvent becomes applied to the absorbent material.

The absorbent component or material such as the test paper can be dried, and the absorbent material containing the dried reagent can be assembled into a diagnostic test device such as a diagnostic test strip. The diagnostic test device can then be used in detecting the presence of an analyte(s) in organic solvents, aqueous solvents, and mixtures thereof. When the diagnostic test device is dipped into a test sample according the methods described herein, the reagent becomes dissolved into the test sample and becomes available to react with the analyte(s) in the test sample. As an increased amount of reagent may be applied to the absorbent component or material by forming the salt complex, an increased amount of reagent is available to become dissolved in the test sample and to detect the presence of an analyte(s) using the methods described herein. Hence, the instrumentally or visually detectable signal to the user (i.e., the change in color) is generally enhanced using the methods described herein and the diagnostic test devices prepared by the methods described herein.

The organic reagent to be applied to the diagnostic test device is generally an organic acid. The organic reagent serves as a source of anions for creating the salt complex. The amine to be used in promoting the solubility of the organic reagent serves as a source of positive counterion(s) which counter the negative charge provided by the anion(s) of the organic reagent. The charges on the anions and cations may be countered such that a salt complex having no net charge may be formed.

The processes and products described herein offer numerous advantages. By using the methods and products described herein, an organic reagent can be applied to a diagnostic test device via organic solvents, aqueous solvents, and mixtures thereof where the reagent would normally be soluble in only organic solvents or in only aqueous solvents. This process improves the ability to absorb organic reagents having no transolubility or only limited transolubility in organic solvents, aqueous solvents, and mixtures thereof into diagnostic test devices using organic solvents, aqueous solvents, and mixtures thereof. By using the methods and products described herein, an organic reagent which would normally be soluble only in organic test samples or only in aqueous test samples may be used to detect the presence of an analyte(s) in organic test samples, aqueous test samples, and mixtures thereof.

A further advantage of the methods and products described herein is that the methods and products allow users to generally control the degree of solubility of the resulting salt complex in a particular solvent and the availability of the organic reagent that is applied to an absorbent component or material such as test strip paper to react with test samples. The amount and the timing of the uptake of a reagent into the absorbent material can be controlled as well as the release or availability of the reagent for reaction with analyte(s) in test samples. By selecting particular mixtures of organic reagents and amines, the salt complex may be designed to be more or less soluble in particular solvents where so desired. For example, by selecting a tri-n-octylamine for salting as compared to tri-ethylamine, a user may render an aryl sulfonate reagent more soluble in an organic solvent. The degree of solubility of a salt complex in organic solvents, aqueous solvents, and/or mixtures thereof can be generally controlled by selecting counterions to the reagent of interest which have greater or lesser aqueous or non-aqueous affinity. Those salts with greater aqueous affinity have increased hydrophilic character. Those salts with greater affinity for non-aqueous solvents have increased lipophilic character.

A further advantage of the methods and products described herein is that the methods and products allow users to generally alter the selectivity of the desired reagent in its interaction with the analyte(s) in the test sample. For example, where the final protein-indicating reaction is dependent upon interaction of the organic reagent with one or more proteins, the sites of these interactions have lipophilic and hydrophilic features with differing degrees of affinity for the salt complexes formed from the lipophilic or hydrophilic counterions.

Suitable organic reagents for use in embodiments of the invention have structural characteristics that allow compatible interactions of the acidic reagent with the anion of the amine such that the salt complex that is formed will be soluble in organic solvents, aqueous solvents, and mixtures thereof. Where a user desires to increase the solubility of an organic reagent in organic solvents, the user may wish to select a reagent having highly aliphatic or aromatic substituent groups with lipophilic character such as alkyl, halogenated alkyl, aryl, or phenyl groups. Where a user desires to increase the solubility of an organic reagent in aqueous solvents, the user may wish to select a reagent having functional groups with hydrophilic properties such as —$(CH_2)_n$—OH, —$(CH_2)_n$—C(O)$NH_2$, —$(CH_2)_n$—SH, or —$CH_2CH_2$—$(OCH_2CH_2)_n$OH groups where n is zero or a positive integer. As used herein, the terms "lipophilic" and "hydrophobic" are synonymous and the terms "lipophobic" are "hydrophilic" are synonymous.

The organic reagents used to form the salt complex are typically organic acids. Suitable organic acids include, but are not limited to, carboxylic, sulfonic, and phosphoric acids having —COOH, —$SO_3H$, and —$OPO_3H$ functional groups respectively, although it is contemplated that any organic molecule which is capable of providing an ionizable group of sufficient acidity to form a salt complex when combined with an amine containing a lipophilic group may be used. Examples of suitable organic reagents include dyes such as pyrogallol red and substituted phenolsulfonephthaleins.

Other suitable dyes include, but are not limited to, acid alizarin violet N, acid blacks, acid blues, acid oranges, acid greens, acid reds, acid violets, acid yellows, alizarin red S, alizarin violet 3R, alizarin yellow GG, alphazurine A, amaranth, 8-anilino-1-sulfonic acid (ANS), arsenazo dyes, aurintricarboxylic acid, azocarmine B, benzopurpurin, biebrich scarlet, bordeaux R, brilliant black BN, brilliant blue G, brilliant blue R, brilliant sulfaflavine, brilliant yellow, bromochlorophenol blue, bromocresol green, bromocresol purple, bromophenol blue, bromopyrogallol red, bromothymol blue, bromoxylenol blue, chicago sky blue 6B, chlorophenol red, chromotrope dyes, chromoxane cyanine R, chysophenine, cibacron brilliant red 3B-A, cibacron brilliant yellow 3G-P, cibacron blue 3G-A, congo red, cresolphthalein, cresol purple, cresol red, direct red 75, direct red 81, dinitrohexabromosulfonephthalein, eosin B, eosin Y, eriochrome black T, eriochrome blue black 2B, eriochrome red B, erioglaucine, erythrosin B, ethyl orange, evans blue, fast green FCF, fast yellow, flavazin L, fluorescein, fluorescein water soluble, 2-(4-hydroxyphenylazo)benzoic acid (HABA), 8-hydroxyquinoline-5-sulfonic acid, indigo carmine, indigotrisulfonic acid, indocyanine green, lucifer yellow, merbromin, metanil yellow, methyl orange, methyl red, methylthymol blue, mordant oranges, mordant red, mordant yellows, naphthochrome green, naphthol AS BI phosphate, naphthol blue black, naphthol yellow S, new coccine, nickel phthalocyaninetetrasulfonic acid, nitrazine yellow, nitro red, nitrosonaphtholdisulfonic acid, nuclear fast red, orange G, orange II, palatine chrome black 6BN, patent blue VF, phenolphthalein, phenol red, phloxine B, plasmocorinth B, ponceau S, ponceau SS, primulin, pyrocatechol violet, rosolic acid, rose bengal, tartrazine, tetrabromophenol blue, tetrabromophonolphthalein, tetrabromophenolsulfonephthalein, thymol blue, thymolphthalein, thymolphthalein monophosphoric acid, tiron, tropaeolin O, trypan blue, violamine R, xylenol blue, xylidyl blue, and zincon. Mixtures of one or more compatible organic reagents may be used in the methods and products described herein. When the organic acid reagent is a dye, it commonly serves as a source of anions for forming the salt complex.

The anionic structures of some of the suitable dyes for use in embodiments of the invention are shown as Structures A-E below. The first ionization form of bromocresol green that is useful in the present invention is represented by Structure A.

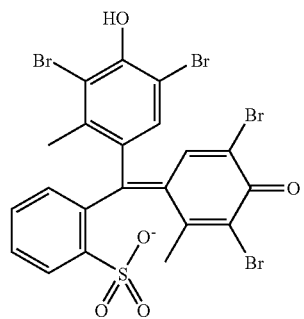

Structure A

The first ionization form of eosin Y that is useful in the present invention is represented by Structure B.

Structure B

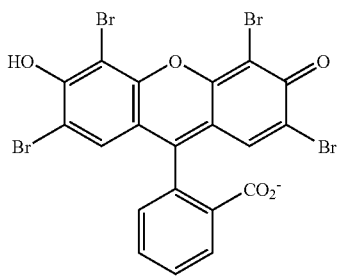

The first ionization form of erythrosin B that is useful in the present invention is represented by Structure C.

Structure C

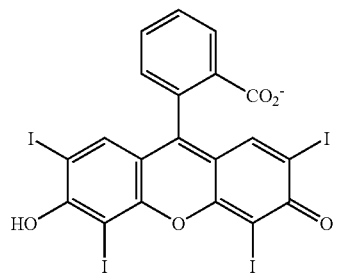

The first ionization form of pyrogallol red that is useful in the present invention is represented by Structure D.

Structure D

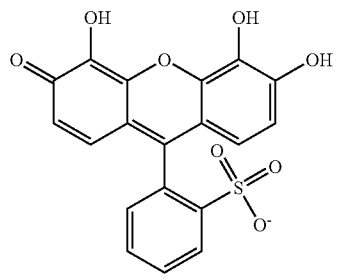

The first ionization form of rosolic acid that is useful in the present invention is represented by Structure E.

Structure E

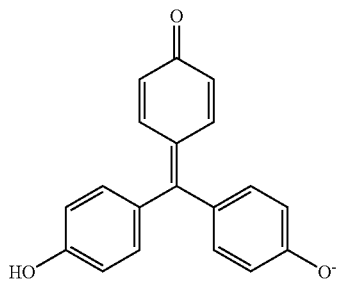

The amines used to form the salt complex have structural characteristics which allow compatible interactions of the cation such that the resulting salt complex will be soluble in organic solvents, aqueous solvents, and mixtures thereof. The amine is chosen to impart some lipophilicity to the salt complex which has some hydrophilic character. Where a user desires to increase the solubility of an organic reagent in an aqueous solvent, the user may wish to select an amine having structural characteristics which enhance ionization, polarization, or hydrogen bonding such as R groups which contain —OH, —SH, —C(O)NH$_2$, hydroxyalkyl, hydroxyalkoxyalkyl, and/or —CH$_2$CH$_2$O)$_n$ functionality. Where a user desires to increase the solubility of an organic reagent in an organic solvent, the user may wish to select an amine having commonly recognized lipophilic features such as alkyl, alkenyl, alkynyl, haloalkyl, aromatic, or haloaromatic functional groups. The choice of counterion structure may also allow a user to inhibit precipitation or crystallization through interaction of the R groups with the solvent.

The amine is the source of the cations for forming the salt complex upon pairing with the anions provided by the organic reagent source. Suitable amines for use in embodiments of the invention generally have the following formula:

$$H_m NR_n.$$

The amine may be in a form having no net charge where m is 0, 1 or 2; n is 1, 2, or 3; and the sum of m and n is 3. The amine may also be in the ammonium form, where the value of m is increased by 1. The amine may further be in the charged quaternary form where n is 4 and m is equal to zero. R is an independently selected group, meaning that R may be the same or different when n is greater than 1. The amines used in forming the salt complex according to the present methods and products may have lipophilic properties, hydrophilic properties, or both lipophilic and hydrophilic properties.

Where a charged quaternary amine is used as the source of the cations for forming the salt complex, an ionized organic reagent such as an organic acid reagent and a quaternary ammonium ion may be combined to form a salt complex where the ammonium ion is represented by the formula $$NR_4^+.$$

R is an independently selected group, meaning that R may be the same or different. The charged quaternary amines used in forming the salt complex according to the present methods and products may have lipophilic properties, hydrophilic properties, or both lipophilic and hydrophilic properties.

The ionized organic reagent and the quaternary ammonium ion may be combined through a variety of methods known in the art such as by an ion exchange process. For example, ion exchange can be performed using batch mode or column mode employing ion exchange media such as resin or carbohydrate with ionizable groups. A typical ion exchange process for an organic acid may begin with loading the organic acid at an ionizing pH or as a salt, such as sodium, onto a prepared column of anion ion exchange media in a suitable form, such as hydroxide, to bind the organic acid to the column. A solution of a quaternary ammonium salt such as tetraethylammonium chloride may then be applied to the column. As the chloride ion displaces the organic acid anion and releases the organic acid anion from the column media, the remaining quaternary ammonium ion pairs with the ionized organic acid, allowing a solution of the quaternary ammonium salt of the organic acid to elute from the column.

The desired degree of solubility of the salt complex may vary based upon the type of solvent(s) required for the particular manufacturing process and the ultimate function of the final product. For example, a particular protein dye may need to be soluble in an aqueous solvent (i.e., a solvent having a high water content) for one step of a manufacturing dip process but insoluble in the organic solvent of a subsequent step to inhibit the dye from washing out in the organic solvent. For medical diagnostics, the dye salt generally needs to possess some aqueous solubility in order to be available for chemical reactions with a biological sample such as urine. Further, the dye salt may have functions such as a color change upon binding to protein that can be preserved or enhanced due to attraction to the lipophilic or hydrophilic portion of the protein. The amine that is used to form the salt complex may impart these solubility and compatibility properties to the dye.

The selection of a suitable R group(s) for use in the amine generally depends on the desired degree of solubility of the amine in the respective organic solvent, aqueous solvent, or mixture thereof. Beginning with n=0 and m=3, amines generally have hydrophilic character. The R group(s) and the number of R group(s) may be selected to maintain the hydrophilic character of the amine or to add lipophilic character to the amine.

R is selected to provide sufficient lipophilicity or hydrophilicity to the amine such that the resulting salt complex is soluble in the desired organic solvent, aqueous solvent, or mixture thereof and to allow compatible interactions of the salt complex with the organic solvent, aqueous solvent, or mixture thereof. R is selected to render the salt complex soluble in aqueous solvents, organic solvents, and mixtures thereof. The desired solubility properties provided by R may be implied from such data as octanol/water partition coefficients for such substances as RH or ROH. In some embodiments, R may be a substituent group having both lipophilic and hydrophilic properties. In other embodiments, at least one R group provides sufficient lipophilicity to render the salt complex soluble in an organic solvent and sufficient hydrophilicity to render the salt complex soluble in an aqueous solvent or a mixture of an aqueous solvent and an organic solvent. R may be selected from, but is not limited to, alkyl, alkenyl, alkynyl, haloalkyl, aromatic, haloaromatic, alkylaminoacetyl, hydroxyalkyl, and hydroxyalkoxyalkyl substituent groups.

The selection of the value of m and n for use in the amine generally depends upon the degree of hydrophilicity of the R group(s) which are selected and the reactivity of the amine toward other reagents. For example, where n=0, 1, or 2, the amine may participate in some nucleophilic reactions. If the user desires to increase the solubility of the organic reagent to be applied to the diagnostic test device in an organic solvent, the user may wish to select an amine with a hydrophobic substituent(s) having a higher value for n such as n=3 in trioctylamine. It is expected that the hydrophobic character of the salt complex will generally increase with increasing hydrophobic character of the R group(s). For example, where R is changed from ethyl to butyl, the hydrophobic character of the salt complex will generally increase whereas where R is changed from octyl to butyl, the hydrophobic character of the salt complex will generally decrease.

Examples of suitable amines for use in embodiments of the invention include, but are not limited to, trimethylamine, triethylamine, tributyl amine, trioctylamine, tris(hydroxymethyl)aminomethane (TRIS), aminoethanol, butylamine, octylamine, triethanolamine, glucamine, polyethyleneglycolamines, amino acids, and mixtures thereof. In some embodiments, tris(hydroxymethyl)aminomethane (TRIS) is used. Although not critical to its use, it is believed that the hydroxy groups in TRIS are compatible with aqueous solvents and that the —CH$_2$OH groups also possess alkyl character which is compatible with organic solvents such as methanol.

Where a charged quaternary amine is used in embodiments of the invention, suitable quaternary ammonium salts include, but are not limited to, tetrabutylammonium hydroxide, tetramethylammonium hydroxide, tetraethylammonium hydroxide, tetraproylammonium hydroxide myristyltrimethylammonium bromide, cetyltrimethylammonium bromide, phenyltrimethylammonium bromide, tetrapentylammonium bromide, tetrahexylammonium bromide, tetraheptylammonium bromide, tetraoctylammonium bromide, and tetraoctadecylammonium bromide.

Examples of suitable quaternary ammonium ions for use in embodiments of the invention include, but are not limited to, tetrabutylammonium, tetramethylammonium, tetraethylammonium, tetraproylammonium myristyltrimethylammonium, cetyltrimethylammonium, phenyltrimethylammonium, tetrapentylammonium, tetrahexylammonium, tetraheptylammonium, tetraoctylammonium, and tetraoctadecylammonium.

The ionic structures of some of the suitable amines for use in embodiments of the invention are shown as Structures F-J below. A trioctylammonium ion that is useful in the present invention is represented by Structure F.

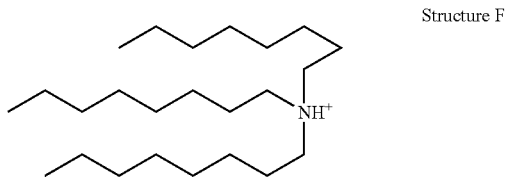

Structure F

A triethylammonium ion that is useful in the present invention is represented by Structure G.

Structure G

A triethanolammonium ion that is useful in the present invention is represented by Structure H.

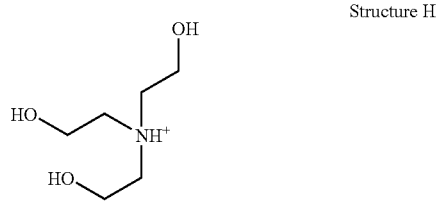

Structure H

An ammonium form of TRIS that is useful in the present invention is represented by Structure I.

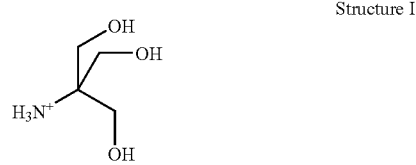

Structure I

A glucammonium ion that is useful in the present invention is represented by Structure J.

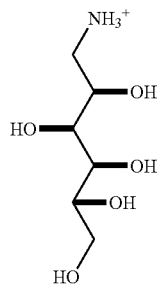

Structure J

Once the salt complex is formed by the steps described above, the salt complex is dissolved in an organic solvent, an aqueous solvent, or a mixture of one or more organic solvents and one or more aqueous solvents. An example of a mixture of one or more organic solvents and one or more aqueous solvents is a mixture of an alcohol and water. By dissolving the salt complex in an organic solvent, an aqueous solvent, or mixtures of one or more organic solvents and one or more aqueous solvents, the reagent may be released into the solvent. The salt complex formed by mixing the organic reagent and the amine is generally soluble in a wider range of solvents than the unsalted organic reagent would be alone.

Examples of suitable organic solvents in which the salt complex may be dissolved include, but are not limited to, alcohols, tetrahydrofuran (THF), and mixtures of toluene and THF. Examples of suitable aqueous solvents in which the salt complex may be dissolved include, but are not limited to, water and mixtures of alcohol and water. Examples of suitable solvents for a multiple-dip application process such as a two-dip application include, but are not limited to, an alcohol-water mixture and a THF-toluene mixture.

Upon dissolving the salt complex in the desired solvent, the reagent is released into the solvent. When a user then dips an absorbent material such as paper into the desired solvent, the reagent that is present in the solvent becomes absorbed into the absorbent material. Users can generally control the degree of reagent solubility in the solvent or test sample by selecting a particular amine and a particular organic reagent such that the resulting salt complex has the desired degree of solubility in organic solvents, aqueous solvents, and mixtures thereof. The methods described herein and the diagnostic test devices prepared by the methods described herein allow users to generally control the degree of reagent solubility in the various dip solutions of a multiple dip application process.

Once the reagent has been absorbed into the absorbent component by the methods described above, the absorbent component is dried and assembled into a diagnostic test device such as a diagnostic test strip for use in detecting the presence of an analyte(s) in organic test samples, aqueous test samples, and sample mixtures of one or more organic solvents and one or more aqueous solvents. Examples of suitable test samples include body fluids and diluted aqueous mixtures thereof.

The following examples are given to exemplify embodiments of the invention. These examples should not be construed to limit the invention as otherwise described and claimed herein.

EXAMPLE 1

A first aqueous solution was formed by the addition of three submixes (Submixes 1-3). To form Submix 1, 10 ml of methanol, 1.76 ml of 125 mM tris(hydroxymethyl)aminomethane (TRIS) in methanol and 44.0 mg of pyrogallol red were added together. These components were mixed for about 20 to about 30 minutes to form Submix 1. To form Submix 2, 4.10 g (3.20 mL) of 40% phytic acid, 8.00 mL of 5% aqueous PVA (polyvinyl alcohol) of 31-50K, 11.2 mL of 1N NaOH, 0.654 mL of 100 mg/mL of aqueous sodium molybdate, and 45.6 mL of water were added together. The NaOH was added to adjust the pH to approximately 2.3. These components were mixed for about 60 minutes to form Submix 2. To form Submix 3, 217.5 mg of disodium oxalate, 120.0 mL of 500 mM L-citrulline with a pH 2.5 and 100.0 mg of Cibacron Brilliant Yellow were added together. The components were mixed for about 30 minutes to form Submix 3.

Submix 1 and Submix 2 were mixed together for about 10 minutes. Next, Submix 3 was added to the combination of Submix 1 and Submix 2 and was mixed until uniform. The mixture of Submixes 1, 2, and 3 was adjusted to pH 2.6. Submixes 1-3 were used to form a First Dip solution adjusted with water to a volume of 200 mL.

The reagent paper was dipped into the First Dip solution of 200 mL and dried in a three-stage tunnel oven at 50/50/70° C. with a 1 inch air flow. The reagent paper used was made from 4 inch Ahlstrom 204 paper.

The Second Dip solution was made by the following procedure. 0.48 g of KOK (a polypropyleneglycol carbonate polymer) such as disclosed in U.S. Pat. No. 5,424,215 was weighed directly into a beaker. Then, 36.57 mg of DNHB (5,5" Dinitro -3',3",3,4,5,6-hexabromophenolsulfonephthalein) was added to the container containing KOK. 16 mL of stabilized THF was added to the mixture of KOK and DNHB in a fume hood. 144 mL of toluene was added to the mixture of KOK, DNHB, and THF and mixed until homogenous to form the Second Dip solution. The Second Dip solution was stable for 24 hours.

The reagent paper was then dipped into the Second Dip solution of 160 mL. The diagnostic reagent paper was dried in a three-stage tunnel oven at 50/50/70° C. with a 1 inch air flow. The paper was cut to form the active pad of the diagnostic test strips. The diagnostic strips included the active pad that was adhered to a polymeric strip.

EXAMPLE 2

Five 5 mM solutions of the dyes listed in Tables 1-5 (i.e., bromocresol green, eosin Y, rosolic acid, 8-anilino-1-sulfonic acid, erythrosin B) in 96% methanol, 2% ethanol and 2% water were prepared. The five dye solutions were then treated with 1 equivalent of each base listed in Tables 1-5 (i.e., sodium hydroxide, TRIS, and triethylamine) to form salt solutions (i.e., sodium salt solutions, TRIS salt solutions, and triethylamine salt solutions respectively).

A 50 µL portion of each salt solution was then mixed with 950 µL water and 1000 µL butanol. Extractions were then performed in Mixxor extractors available from Aldrich Chemical Company. Where necessary to deal with lingering interface phases, the samples were centrifuged.

Tests were then performed on the respective salt solutions to determine whether the salts of the respective dyes dissolved preferentially in butanol (a more lipophilic solvent) or water (a less lipophilic solvent). The ratio of the dye concen tration for the butanol layer versus the water layer was determined by spectroscopy using a Hewlett Packard 8453 diode array spectrophotometer and a 1 mL quartz cuvette. Spectroscopy versus the butanol blank or the water blank was done as 50 μL upper (butanol) or lower (aqueous) phase plus 950 μL corresponding solvent. All absorbances were blanked on solvent in a quartz cuvette and were baseline corrected at an absorbance of 900 nm before subsequent calculations to correct for cuvette placement, dust, etc. All absorbances were then measured at the wavelengths noted below.

Before determining the butanol to water absorbance levels, the absorbance of the solute in butanol was corrected for solvent dependent shifts in wavelength maximum and intensity based on the reference spectra of known gravimetric quantities of the dye salts in butanol and water. For such cases, the partition ratio of butanol absorbance to water absorbance was calculated using the following formula:

Partition Ratio=Sample Absorbance in Butanol×Intensity Factor/Sample Absorbance in Water where the intensity factor was calculated using the following formula:

Intensity Factor=Reference Sample Absorbance at $\lambda_{max}$ in water/Reference Sample Absorbance at $\lambda_{max}$ in butanol The intensity factor adjusts for those cases where the same concentration of dye in the two different solvents produced two different absorbances.

The water absorbances, butanol absorbances, intensity factors, raw absorbance ratios, and partition ratios of the respective salt solutions are shown below in Tables 1-5.

TABLE 1

Butanol/Water Partitioning of Bromocresol Green Salts

| Base | Absorbance of Base in Water[1] | Absorbance of Base in Butanol[2] | Intensity Factor (IF) | Raw Ratio of Butanol Absorbance to Water Absorbance | Partition Ratio of Butanol Absorbance to Water Absorbance |
|---|---|---|---|---|---|
| Sodium Hydroxide | 0.175 | 0.315 | 1.03 | 1.8 | 1.9 |
| TRIS | 0.146 | 0.250 | 2.47 | 1.7 | 4.2 |
| Triethylamine | 0.097 | 0.237 | 2.58 | 2.4 | 6.3 |

[1]The wavelength ($\lambda_{max}$) was 615 nm.
[2]The wavelength ($\lambda_{max}$) was 630 nm.

TABLE 2

Butanol/Water Partitioning of Eosin Y Salts

| Base | Absorbance of Base in Water[3] | Absorbance of Base in Butanol[4] | Intensity Factor (IF) | Raw Ratio of Butanol Absorbance to Water Absorbance | Partition Ratio of Butanol Absorbance to Water Absorbance |
|---|---|---|---|---|---|
| Sodium Hydroxide | 0.700 | 0.128 | 1.04 | 0.18 | 0.19 |
| TRIS | 0.703 | 0.174 | 1.00 | 0.25 | 0.25 |
| Triethylamine | 0.705 | 0.187 | 0.99 | 0.26 | 0.26 |

[3]The wavelength ($\lambda_{max}$) was 518 nm.
[4]The wavelength ($\lambda_{max}$) was 530 nm.

TABLE 3

Butanol/Water Partitioning of Rosolic Acid Salts

| Base | Absorbance of Base in Water[5,6] | Absorbance of Base in Butanol[7] | Intensity Factor (IF) | Raw Ratio of Butanol Absorbance to Water Absorbance | Partition Ratio of Butanol Absorbance to Water Absorbance |
|---|---|---|---|---|---|
| Sodium Hydroxide | 0.085 | 0.147 | 0.69 | 1.7 | 1.2 |
| TRIS | 0.003 | 0.055 | 1.07 | 17 | 18 |
| Triethylamine | 0.006 | 0.077 | 0.94 | 12 | 11 |

[5]The wavelength ($\lambda_{max}$) was 547 nm.
[6]Due to the strong solvent dependent spectral intensity and predominant butanol partitioning of the rosolic acid salt, the aqueous solvent for the reference sample of rosolic acid salt was saturated with butanol before measuring its absorbance. The absorbance of the aqueous layer in the case of the rosolic acid salt was very weak so a solution that was four times less dilute was measured. Thus, the aqueous absorbances shown in Table 3 above have been divided by four.
[7]The wavelength ($\lambda_{max}$) was 562 nm.

TABLE 4

Butanol/Water Partitioning of 8-Anilino-1-Sulfonic Acid Salts

| Base | Absorbance of Base in Water[8] | Absorbance of Base in Butanol[9] | Intensity Factor (IF) | Raw Ratio of Butanol Absorbance to Water Absorbance | Partition Ratio of Butanol Absorbance to Water Absorbance |
|---|---|---|---|---|---|
| Sodium Hydroxide | 0.065 | 0.121 | 0.98 | 1.9 | 1.8 |
| TRIS | 0.050 | 0.129 | 0.89 | 2.6 | 2.3 |
| Triethylamine | 0.045 | 0.156 | 1.01 | 3.4 | 3.5 |

[8]The wavelength ($\lambda_{max}$) was 265 nm.
[9]The wavelength ($\lambda_{max}$) was 269 nm.

TABLE 5

Butanol/Water Partitioning of Erythrosin Salts

| Base | Absorbance of Base in Water[10] | Absorbance of Base in Butanol[11] | Intensity Factor (IF) | Raw Ratio of Butanol Absorbance to Water Absorbance | Partition Ratio of Butanol Absorbance to Water Absorbance |
|---|---|---|---|---|---|
| Sodium Hydroxide | 0.574 | 0.237 | 0.93 | 0.41 | 0.38 |
| TRIS | 0.631 | 0.196 | 0.90 | 0.31 | 0.28 |
| Triethylamine | 0.596 | 0.240 | 1.04 | 0.40 | 0.42 |

[10]The wavelength ($\lambda_{max}$) was 528 nm.
[11]The wavelength ($\lambda_{max}$) was 536 nm.

The data set forth in Tables 1-5 above shows that higher ratios of partitioning of the respective dye salts in the butanol layer versus the water layer were obtained with triethylamine, the most lipophilic of the amines tested. These results indicate that the salt became more lipophilic in the presence of the triethylammonium cation, enabling more of the salt to dissolve in the butanol layer, the more lipophilic solvent.

EXAMPLE 3

A solution of pyrogallol red at 2 mg/mL in methanol with 2% ethanol and 2% water was prepared. The pyrogallol red solution was then treated with one equivalent of each base listed in Table 6 (i.e., triethanolamine, glucamine, sodium hydroxide, trioctylamine, TRIS, and triethylamine) to form the respective pyrogallol red salt solutions (i.e., triethanolamine salt solution, glucamine salt solution, sodium salt solution, trioctylamine salt solution, TRIS salt solution, and triethylamine salt solution respectively).

Aliquots of 50 μL of each pyrogallol red salt solution were then mixed with 950 μL water and 1000 μL butanol. Extractions were then performed in Mixxor extractors.

Tests were then performed on the respective salt solutions to determine whether the salts of the pyrogallol red dye dissolved preferentially in butanol (a more lipophilic solvent) or water (a less lipophilic solvent). The ratio of the dye concentration for the butanol layer versus the water layer was determined by spectroscopy using a Hewlett Packard 8453 diode array spectrophotometer and a 1 mL quartz cuvette. Spectroscopy versus the butanol blank or the water blank was done as 50 μL upper (butanol) or lower (aqueous) phase plus 950 μL corresponding solvent. All absorbances were blanked on solvent in a quartz cuvette and were baseline corrected at an absorbance of 900 nm before subsequent calculations to correct for cuvette placement, dust, etc. and were then measured at 276 nm.

TABLE 6

Butanol/Water Partitioning of Pyrogallol Red Dye Salts of Various Bases

| Base | Absorbance of Dye Salt in Butanol | Absorbance of Dye Salt in Water | Ratio of Butanol Absorbance to Water Absorbance |
|---|---|---|---|
| Triethanolamine | 0.044 | 0.296 | 0.15 |
| Glucamine | 0.030 | 0.328 | 0.09 |
| Sodium Hydroxide | 0.034 | 0.338 | 0.10 |
| Trioctylamine | 0.155 | 0.049 | 3.17 |
| TRIS | 0.041 | 0.326 | 0.13 |
| Triethylamine | 0.063 | 0.274 | 0.23 |

The data set forth in Table 6 above shows that higher ratios of partitioning of the respective dye salts in the butanol layer versus the water layer were obtained with trioctylamine, the most lipophilic of the amines tested. These results indicate that the salts became more lipophilic in the presence of the trioctylammonium cation, enabling more of the salt to dissolve in the butanol layer, the more lipophilic solvent.

EXAMPLE 4

A solution of pyrogallol red at 2 mg/mL in methanol with 2% ethanol and 2% water was prepared. The pyrogallol red solution was then treated with one equivalent of the following amines: TRIS, triethanolamine, glucamine, triethylamine, trioctylamine, and sodium to form the respective pyrogallol red salt solutions listed in Table 7 (i.e., TRIS salt solution, triethanolamine salt solution, glucamine salt solution, triethylamine salt solution, trioctylamine salt solution, and sodium salt solution respectively).

Aliquots of 100 μL of each pyrogallol red salt solution were then mixed with solutions of 0 to 100 μL toluene and methanol for the remainder to make 1000 μL solutions. Toluene is a non-polar, organic solvent which is generally lipophilic. The 1000 μL solutions were allowed to form precipitate by standing overnight in sealed vials. The samples were then centrifuged.

The fluid portions of the centrifuged samples were then analyzed by spectroscopy. An analysis of the ratio of the concentration of the respective salt solutions in toluene was measured against a methanol blank. This analysis was performed to determine the solubility threshold of pyrogallol red salts in solvent having an increasing percentage of toluene. The solubility of the fluid portions of the centrifuged samples was determined spectroscopically using a Hewlett Packard 8453 diode array spectrophotometer and a 1 mL quartz cuvette. Spectroscopy versus the methanol blank was conducted as 50 μL fluid plus 950 μL methanol. The percent recovery of the spin supernates (i.e., how much of the pyrogallol red salt remained in solution) was determined at an absorbance of 518 nm and was compared to the absorbance level of a solution containing no toluene, which provided complete and stable solubility (100% recovery) of all of the salts.

TABLE 7

Stability of Pyrogallol Red in Solvents of Increasing Lipophilicity as Percent Recovery of Absorbance

| Percent Toluene | TRIS Salt | Triethanolamine Salt | Glucamine Salt | Triethylamine Salt | Trioctylamine Salt | Sodium Salt |
|---|---|---|---|---|---|---|
| 0 | 100 | 100 | 100 | 100 | 100 | 100 |
| 20 |  |  |  |  |  | 81 |
| 40 |  |  |  |  |  | 88 |
| 60 |  |  | 85 |  |  | 81 |
| 70 | 99 |  | 84 |  |  | 101 |
| 75 |  |  | 58 |  |  | 103 |
| 80 | 97 | 95 | 44 | 101 | 103 | 68 |
| 83 | 98 |  |  |  |  |  |
| 85 |  | 46 | 23 |  |  | 61 |
| 86 |  |  |  | 96 |  |  |
| 87 | 20 | 19 | 15 |  | 97 |  |
| 88 |  | 36 |  |  | 99 |  |
| 89 | 1 | 23 | 7 |  | 100 |  |
| 90 | 16 | 7 | 5 | 101 | 91 | 4 |

\* The shaded entries in Table 7 above represent the proportions of toluene in solvent where each salt remained soluble overnight.

The data set forth in Table 7 above shows the stability of pyrogallol red in solvents having increasing lipophilicity represented as the percent recovery of solution absorbance. The data set forth in Table 7 above shows that the more lipophilic cations such as those from TRIS, triethylamine, and trioctylamine enabled more of the pyrogallol red dye salt to remain in a solution having a high content of a non-polar, organic component such as toluene.

EXAMPLE 5

An automated protein assay was devised for the BioTek, Precision 2000 96/384 Well Microplate Automated Pipetting System to determine the relative detection of different proteins using salts of pyrogallol red. The dilutor was programmed for reactions of 180 µL reagent+40 µL sample. The reagent was 250 mM citrulline buffer (at pH 2.5) with 160 µM molybdate and 54 µM pyrogallol red salt. The samples were phosphate buffered saline (blank), human serum albumin (HSA) 25 mg/dL, and other proteins (i.e., human IgG, Tammm-Horsfall, and Lambda Light Chain) at 25 mg/dL.

Absorbance rate data were collected on a Biotek, Powerwave X Microplate Absorbance reader using BioTek "KC Jr" software to determine the relative detection of the different proteins (i.e., HSA, human IgG, Tammm-Horsfall, and Lambda Light Chain) using salts of pyrogallol red. Two sets of replicates of the different proteins were run. The absorbance was measured at 600 nm (the absorbance frequency of blue colors), and the baseline absorbance at 900 nm (an absorbance frequency beyond the visible range) was subtracted after 10 minutes at 37° Centigrade. The protein response was determined by subtracting the phosphate buffered saline sample reaction result from the protein reaction result. The net absorbance at 600 nm and at 900 nm at 10 minutes reaction time is shown below in Table 8.

TABLE 8

Reaction Absorbances at 10 Minutes Reaction Time

| Protein | Sodium Pyrogallol Red Salt in Phosphate Buffered Saline (No Protein) | Sodium Pyrogallol Red Salt with Protein | Trioctylamine Pyrogallol Red Salt in Phosphate Buffered Saline (No Protein) | Trioctylamine Pyrogallol Red Salt with Protein |
|---|---|---|---|---|
| 600 nm Absorbance Levels | | | | |
| REPLICATE #1 | | | | |
| HSA | 0.197 | 0.211 | 0.476 | 0.454 |
| IgG | 0.199 | 0.207 | 0.482 | 0.475 |
| Tamm-Horsfall | 0.196 | 0.203 | 0.485 | 0.454 |
| Lambda Light Chain | 0.198 | 0.204 | 0.485 | 0.446 |
| REPLICATE #2 | | | | |
| HSA | 0.196 | 0.211 | 0.483 | 0.464 |
| IgG | 0.200 | 0.208 | 0.489 | 0.474 |
| Tamm-Horsfall | 0.198 | 0.204 | 0.486 | 0.45 |
| Lambda Light Chain | 0.196 | 0.201 | 0.485 | 0.44 |
| 900 nm Absorbance Background Levels | | | | |
| REPLICATE #1 | | | | |
| HSA | 0.035 | 0.035 | 0.082 | 0.087 |
| IgG | 0.036 | 0.037 | 0.081 | 0.092 |
| Tamm-Horsfall | 0.036 | 0.036 | 0.081 | 0.085 |
| Lambda Light Chain | 0.034 | 0.035 | 0.081 | 0.086 |
| REPLICATE #2 | | | | |
| HSA | 0.035 | 0.035 | 0.081 | 0.088 |
| IgG | 0.036 | 0.036 | 0.082 | 0.093 |
| Tamm-Horsfal | 0.035 | 0.036 | 0.082 | 0.084 |
| Lambda Light Chain | 0.035 | 0.036 | 0.08 | 0.087 |

The net protein response for trioctylamine versus sodium salts of pyrogallol red for the protein samples minus the non-protein samples are shown in Table 9 below. The absorbance at 600 nm at 10 minutes reaction time was corrected by the baseline absorbance at 900 nm and is shown below in Table 9 as averaged data.

TABLE 9

Detection of Proteins by Two Pyrogallol Red Salts

| Protein | Sodium Salt Reaction Absorbance at 600 nm − Absorbance at 900 nm | Trioctylamine Salt Reaction Absorbance at 600 nm − Absorbance at 900 nm |
|---|---|---|
| HSA | 0.015 | −0.021 |
| IgG | 0.008 | −0.011 |
| Tamm-Horsfal | 0.007 | −0.034 |
| Lambda Light Chain | 0.006 | −0.042 |

This experiment showed a modest response to protein from the sodium salt of pyrogallol red. The absorbance at 600 nm for the protein samples ranged from 0.201 to 0.211 while the absorbance at 600 nm for the non-protein sample (i.e., the PBS blanks) was lower, ranging from 0.196 to 0.200. Following the 900 nm absorbance background subtraction, the average difference between the protein and non-protein reactions ranged from 6 to 15 milli absorbance units.

However, the highly lipophilic cation, trioctylammonium, caused an immediate, strong blue color of the pyrogallol red reagent solution in the non-protein blank which was indistinguishable in color from the protein reaction. The absorbance levels of the non-protein blanks were slightly stronger than the absorbance levels of the protein reactions. The blue color of the trioctylammonium pyrogallol red did not dissipate when incubated in the citrulline buffer whether with protein (absorbance at 600 nm=0.44 to 0.48) or without protein (absorbance at 600 nm=0.48 to 0.49). This data suggests that the ion pairs of anionic dye and lipophilic cation may remain associated and stable over moderate periods of time even in the presence of large amounts of sodium cation.

EXAMPLE 6

An automated protein assay was devised for the BioTek, Precision 2000 96/384 Well Microplate Automated Pipetting System to determine the relative detection of different proteins using salts of pyrogallol red. The dilutor was programmed for reactions of 180 μL reagent+40 μL sample. The reagent was 250 mM citrulline buffer (at pH 2.5) with 160 μM molybdate and 74 μM pyrogallol red salt. The samples were phosphate buffered saline (blank), human serum albumin (HSA) 25 mg/dL, and other proteins (i.e., human IgG, Tammm-Horsfall, and Lambda Light Chain) at 25 mg/dL.

Absorbance data were collected on a Biotek, Powerwave X Microplate Absorbance reader using BioTek "KC Jr" software to determine the relative detection of the different proteins (i.e., HSA, human IgG, Tammm-Horsfall, and Lambda Light Chain) using salts of pyrogallol red. Two sets of replicates of the different proteins were run. The absorbance was measured at 600 nm and the baseline absorbance at 900 nm was subtracted after 10 minutes at 37° Centigrade. The protein response was determined by subtracting the phosphate buffered saline sample reaction result from the protein reaction result. The average net absorbance for the two sets of replicates at 600 nm at 10 minutes reaction time after subtracting the phosphate buffered saline (PBS) sample reaction result is shown below in Table 10.

TABLE 10

Detection of Different Proteins by Five Pyrogallol Red Salts

SERIES #1

| Protein | Sodium Pyrogallol Red Salt | TRIS Pyrogallol Red Salt | Triethylamine Pyrogallol Red Salt |
|---|---|---|---|
| HSA | 0.0536 | 0.0750 | 0.0600 |
| IgG | 0.0311 | 0.0410 | 0.0285 |
| Tamm-Horsfall | 0.0141 | 0.0175 | 0.0135 |
| Lambda Light Chain | 0.0041 | 0.0030 | 0.0020 |

SERIES #2

| Protein | Sodium Pyrogallol Red Salt | Glucamine Pyrogallol Red Salt | Triethylamine Pyrogallol Red Salt |
|---|---|---|---|
| HSA | 0.0563 | 0.0618 | 0.0559 |
| IgG | 0.0318 | 0.0318 | 0.0284 |
| Tamm-Horsfall | 0.0118 | 0.0123 | 0.0109 |
| Lambda Light Chain | 0.0037 | 0.0088 | 0.0049 |

The results for protein equivalence of the non-albumin proteins were expressed as a percentage of the protein colorimetric response to HSA as shown in Table 11 below.

TABLE 11

Percent Detection of Different Proteins by Five Pyrogallol Red Salts as Percentage of HSA Detection

SERIES #1

| Protein | Sodium Pyrogallol Red Salt | TRIS Pyrogallol Red Salt | Triethylamine Pyrogallol Red Salt |
|---|---|---|---|
| IgG | 58 | 55 | 48 |
| Tamm-Horsfall | 26 | 23 | 22 |
| Lambda Light Chain | 8 | 4 | 3 |

SERIES #2

| Protein | Sodium Pyrogallol Red Salt | Glucamine Pyrogallol Red Salt | Triethylamine Pyrogallol Red Salt |
|---|---|---|---|
| IgG | 56 | 51 | 51 |
| Tamm-Horsfall | 21 | 20 | 19 |
| Lambda Light Chain | 7 | 14 | 9 |

As shown in Table 11 above, compared to sodium salt, the four salts with more complex cations gave roughly similar results for the IgG and Tamm-Horsfall proteins. The more lipophilic triethylammonium counterion was less responsive (3%) than sodium (8%) to the Lambda Light Chain protein. The more hydrophilic glucammonium cation was more responsive (14%) than sodium (8%) to the Lambda Light Chain protein. The sodium salt of pyrogallol red is known to exhibit different affinity for binding and, therefore, a different detection response to different proteins. Example 6 demonstrates that the relative affinity of ionized dyes for different proteins is affected by the nature of their counterions.

While the invention has been described with a number of embodiments, the scope of the invention is not intended to be limited by the specific embodiments. Modifications and variations from the described embodiments exist. For example, while the invention is described in connection with test samples comprising biological fluids such as human urine, suitable test samples may also include agricultural or environmental fluids.

In addition, although the inventive methods and products have been described in connection with organic acid reagents such as acidic dyes, it is contemplated that the technique may also be applied to an organic-soluble enzyme substrate such as bromo, chloroindolyl phosphate. It is contemplated that an organic-soluble enzyme substrate can also be combined with an amine having the hydrophilic properties discussed above such that an enzyme substrate which is soluble in organic solvents but has no solubility or only limited solubility in aqueous solvents can be rendered soluble in aqueous solvents.

Also, although the inventive methods and products have been described in connection with reagents which are organic acids, it is contemplated that the technique may also be applied to an organic molecule which has groups capable of developing a positive charge, such as an organic amine. For example, an organic amine could be countered with $RSO_3H$ or $ROPO_3H$ or $RCO_2H$ where R is selected based upon the desired hydrophilic or hydrophobic properties in a similar manner as described above.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A method of applying an organic aromatic acid dye other than pyrogallol red having limited solubility in aqueous solvents to a component of a diagnostic test device comprising:
    mixing said organic aromatic acid dye other than pyrogallol red and tris(hydroxyl methyl) amino methane to form a salt complex in solution, said organic aromatic acid dye other than pyrogallol red having at least one functional group selected from a carboxylic acid, a sulfonic acid, a phosphoric acid and a mixture thereof;
    adding the salt complex in solution to a solvent to release the salt complex into the solvent; and
    applying the solvent containing said salt complex to the component of the diagnostic test device such that said salt complex present in the solvent becomes integrated into the diagnostic test device.

2. The method of claim 1, wherein said organic aromatic acid dye is a phenolsulfonephthalein.

3. The method of claim 1, wherein the diagnostic test device is a diagnostic test strip and the component is paper.

4. The method of claim 3, wherein the diagnostic test strip is adapted to detect the presence of an analyte in a fluid.

5. The method of claim 4, wherein the analyte is a protein.

6. A method of applying an organic aromatic acid dye other than pyrogallol red having limited solubility in aqueous solvents to a component of a diagnostic test device comprising:
mixing said organic aromatic acid dye other than pyrogallol red and an amine to form a salt complex in solution, the amine is represented by the formula HmNRn wherein m is 0, 1, or 2; n is 1, 2, or 3; the sum of m and n is 3; and R is an independently selected organic group which renders the salt complex more soluble in aqueous solvents, said organic aromatic acid dye other than pyrogallol red being a phenolsulfonephthalein;
adding the salt complex in solution to a solvent to release the salt complex into the solvent; and
applying the solvent containing said salt complex to the component of the diagnostic test device such that said salt complex present in the solvent becomes integrated into the diagnostic test device.

7. The method of claim 6, wherein the amine is tris(hydroxymethyl)aminomethane.

8. A method of applying an organic aromatic acid dye other than pyrogallol red having limited solubility in aqueous solvents to a component of a diagnostic test device comprising:
mixing an organic aromatic acid dye other than pyrogallol red having at least one functional group selected from a carboxylic acid, a sulfonic acid, a phosphoric acid and a mixture thereof and tris (hydroxylmethyl) methane to form a salt complex in solution;
adding the salt complex in solution to a solvent to release said salt complex into the solvent; and
applying the solvent containing said salt complex to the component of the diagnostic test device such that said salt complex present in the solvent becomes integrated into the diagnostic test device.

9. The method of claim 8, wherein said organic aromatic acid dye is a phenolsulfonephthalein.

10. A method of applying an organic aromatic acid dye other than pyrogallol red having limited solubility in aqueous solvents to a component of a diagnostic test device comprising:
mixing a phenolsulfonephthalein and an amine selected from trimethylamine, triethylamine, tributyl amine, trioctylamine, tris (hydroxymethyl) aminomethane, aminoethanol, butylamine, octylamine, triethanolamine, glucamine, a polyethyleneglycolamine, an amino acid, and mixtures thereof to form a salt complex in solution;
adding the salt complex in solution to a solvent to release said salt complex into the solvent; and
applying the solvent containing said salt complex to the component of the diagnostic test device such that said salt complex present in the solvent becomes integrated into the diagnostic test device.

11. The method of claim 10, wherein the amine is tris (hydroxymethyl)aminomethane.

12. The method of claim 10, wherein the diagnostic test device is adapted to detect the presence of a protein in a fluid.

13. The method of claim 10, wherein the diagnostic test device is a diagnostic test strip and the component is paper.

14. A method of applying an organic aromatic acid dye other than pyrogallol red having limited solubility in aqueous solvents to a paper of a diagnostic test strip comprising:
mixing tris(hydroxymethyl)aminomethane and an organic aromatic acid dye other than pyrogallol red having an acid functional group selected from a carboxylic acid, a sulfonic acid, a phosphoric acid, and mixtures thereof to form a salt complex in solution;
adding the salt complex in solution to a solvent to release said salt complex into the solvent; and
applying the solvent containing said salt complex to the paper of the diagnostic test strip such that said salt complex present in the solvent becomes integrated into the paper.

15. The method of claim 14, wherein the organic aromatic acid dye is a phenolsulfonephthalein.

16. A method of applying an organic aromatic acid dye other than pyrogallol red having limited solubility in aqueous solvents to a paper of a diagnostic test strip comprising:
mixing an amine selected from trimethylamine, triethylamine, tributyl amine, trioctylamine, tris(hydroxymethyl)aminomethane, aminoethanol, butylamine, octylamine, triethanolamine, glucamine, a polyethyleneglycolamine, an amino acid, and mixtures thereof and a phenolsulfonephthalein to form a salt complex in solution;
adding the salt complex in solution to a solvent to release said salt complex into the solvent; and
applying the solvent containing said salt complex to the paper of the diagnostic test strip such that said salt complex present in the solvent becomes integrated into the paper.

17. The method of claim 16, wherein the amine is tris (hydroxymethyl)aminomethane.

18. A diagnostic test device containing an organic aromatic acid dye other than pyrogallol red having limited solubility in aqueous solvents prepared by the process of
mixing an organic aromatic acid dye other than pyrogallol red and tris(hydroxymethyl)aminomethane, said organic aromatic acid dye having at least one functional group selected from a carboxylic acid, a sulfonic acid, a phosphoric acid and a mixture thereof;
adding the salt complex in solution to a solvent to release said complex into the solvent; and
applying the solvent containing said salt complex to a component of the diagnostic test device such that said salt complex present in the solvent becomes integrated into the diagnostic test device.

19. The diagnostic test device of claim 18, wherein the organic aromatic acid dye is a phenolsulfonephthalein.

20. The diagnostic test device of claim 18, wherein the diagnostic test device is adapted to detect the presence of an analyte in a fluid.

21. The diagnostic test device of claim 20, wherein the analyte is a protein.

22. A diagnostic test device containing an organic aromatic acid dye other than pyrogallol red having limited solubility in aqueous solvents prepared by the process of
mixing an organic aromatic acid dye other than pyrogallol red and an amine to form a salt complex in solution, the amine is represented by the formula HmNRn wherein m is 0, 1, or 2; n is 1, 2, or 3; the sum of m and n is 3; and R is an independently selected organic group which renders the salt complex more soluble in aqueous solvents, said organic aromatic acid dye being a phenolsulfonephthalein;
adding the salt complex in solution to a solvent to release said complex into the solvent; and applying the solvent containing said salt complex to a component of the diagnostic test device such that said salt complex present in the solvent becomes integrated into the diagnostic test device.

23. The diagnostic test device of claim 22 wherein the amine is tris(hydroxymethyl)aminomethane.

24. The diagnostic test device of claim 22 wherein the diagnostic test device is a diagnostic test strip and the component is paper.

* * * * *